(12) United States Patent
Winsor

(10) Patent No.: US 10,111,584 B2
(45) Date of Patent: Oct. 30, 2018

(54) APPARATUS AND METHOD FOR FIXATION MEASUREMENT WITH REFRACTION ERROR MEASUREMENT USING IMAGE SENSING DEVICES

(71) Applicant: REBIScan, Inc., Cambridge, MA (US)

(72) Inventor: Robert Scott Winsor, Round Hill, VA (US)

(73) Assignee: REBISCAN, INC., Cambridge, MA (US)

( * ) Notice: Subject to any disclaimer, the term of this patent is extended or adjusted under 35 U.S.C. 154(b) by 159 days.

(21) Appl. No.: 14/978,865

(22) Filed: Dec. 22, 2015

(65) Prior Publication Data

US 2016/0174832 A1 Jun. 23, 2016

Related U.S. Application Data

(60) Provisional application No. 62/096,036, filed on Dec. 23, 2014.

(51) Int. Cl.
| | |
|---|---|
| *A61B 3/103* | (2006.01) |
| *A61B 3/036* | (2006.01) |
| *A61B 3/00* | (2006.01) |
| *A61B 3/14* | (2006.01) |
| *G02B 3/06* | (2006.01) |
| *G02B 5/10* | (2006.01) |

(52) U.S. Cl.
CPC ............ *A61B 3/0091* (2013.01); *A61B 3/036* (2013.01); *A61B 3/14* (2013.01); *G02B 3/06* (2013.01); *G02B 5/10* (2013.01)

(58) Field of Classification Search
CPC ......... A61B 3/103; A61B 3/1208; A61B 3/12; A61B 3/1015; A61B 3/1005; A61B 3/0091; A61B 3/036; A61B 3/14; A61B 3/06; G02B 5/10
USPC ........................................................ 351/211
See application file for complete search history.

(56) References Cited

U.S. PATENT DOCUMENTS

| | | | |
|---|---|---|---|
| 5,760,943 A | 6/1998 | Kim et al. | |
| 5,963,359 A | 10/1999 | Shinozaki et al. | |
| 6,027,216 A | 2/2000 | Guyton et al. | |
| 6,059,773 A | 5/2000 | Maloney et al. | |
| 2011/0196200 A1* | 8/2011 | Glozman | A61B 1/00096 600/109 |
| 2013/0128225 A1 | 5/2013 | Wall et al. | |
| 2014/0131327 A1 | 5/2014 | Nishitani et al. | |

OTHER PUBLICATIONS

International Search Report and Written Opinion cited in corresponding International Application No. PCT/US15/67444 dated Mar. 10, 2016.

* cited by examiner

*Primary Examiner* — William R Alexander
*Assistant Examiner* — Henry Duong
(74) *Attorney, Agent, or Firm* — Amardeep S. Grewal; Reed Smith LLP

(57) ABSTRACT

A method and apparatus for fixation measurement includes projecting, by a projection apparatus, a target image onto one or more eyes of a patient and capturing, by one or more image sensing devices disposed conjugate to the one or more eyes, a reflected image reflected from the one or more eyes in response to the target image, wherein the reflected image includes information indicating the fixation of the one or more eyes.

24 Claims, 13 Drawing Sheets

APPARATUS AND METHOD FOR FIXATION MEASUREMENT WITH REFRACTION ERROR MEASUREMENT USING IMAGE SENSING DEVICES

RELATED APPLICATION DATA

This application claims priority to U.S. Provisional Application No. 62/096,036, filed Dec. 23, 2014, the disclosure of which is hereby incorporated by reference in its entirety.

BACKGROUND

Within the field of optometry, there exist many devices that are used to assess the direction of fixation of an eye. An example of such a device is described in U.S. Pat. No. 6,027,216, the contents of which are hereby incorporated in their entirety. Many such devices utilize a scanning laser beam to perform measurements.

One example of such a device is shown in FIG. 1. The device includes a light source 101, a beam splitter 102, a polarization beam splitter 103, photodetectors 104A and 104B, a motor 105 having a rotatable shaft, a first concave mirror 106, and a second concave mirror 107.

The light source 101 provides a diverging beam of polarized light which passes through beam splitter 102 and is incident on the first concave mirror 106. The first concave mirror 106 is mounted in a tilted fashion on the shaft of the motor 105 such that the first concave mirror wobbles 106 slightly when the shaft rotates. The first concave mirror 106 forms an image of the light source 101 on the surface of the second concave mirror 107. The second concave mirror 107 is stationary and is larger than the first concave mirror 106. As the shaft of motor 105 rotates, the image of the light source 101 on the surface of second concave mirror 107 is continuously scanned about a circular path. The curvature of stationary second concave mirror 107 can be chosen such that an image reflected from the spinning first concave mirror 106 is formed directly at the eye 108. All the light leaving the spinning first concave mirror 106 is imaged by stationary second concave mirror 107 to pass through a stationary exit pupil of the device, designated by the dashed circle, which overfills the pupil of the eye 108. The eye 108 sees the spinning image of the light source 101 in the form of a circle of light on the surface of stationary second concave mirror 107. A continuous annular scan of retinal areas is thus achieved by the light incident on the eye 108.

In order to allow for rapid measurements of the light reflected from the fundus, it is desirable to operate the above-described scanning at a scanning rate of at least 100 Hz and preferably at rates of 200 Hz or more. Scan rates at 200 Hz or more permit measurements to be obtained when working with subjects that may be less than fully cooperative, as is commonly the case with very young children. Such rates require the mechanical rotation of the first concave mirror 106 at rates which place special requirements on the mounting of the first concave mirror 106 and the motor 105 that spins it. In the case of retinal birefringent scanning, the first concave mirror 106 is tilted at an angle of approximately 1.5 degrees (to generate a tilt of approximately 3 degrees), and the first concave mirror 106 is then rotated about the axis of the chief ray of the optical beam.

Unfortunately, the tilt of the first concave mirror 106 can create a problem when it is rotated at high rates. Although the first concave mirror 106 is mechanically balanced when not rotating, the introduction of spin generates forces on the first concave mirror 106 (and the mechanical apparatus holding the mirror) that are not balanced, resulting in vibrations.

One known approach to minimize excessive vibration with a rotating tilted disk is to use a symmetrical disk which is of the same mass, size and shape of the tilted disk, but angled opposite to the angle of the tilted disk.

There are still potential shortcomings with this approach. Most notable is that the mass of the rotating object has doubled. For a device that performs scanning, this places extra time delay between the time when the motor is started and the time when the needed rotational speed has been achieved. This can make the device unsuitable for stopping and starting, and may require that the device is simply left with the motor spinning so that it is ready to use. Another potential shortcoming with this approach is that the tilted disk may have a shape that is not a simple flat disk but rather a concave disk such as the first concave mirror of the '216 patent. In this situation, a symmetrical concave mirror could be tilted at precisely the same angle (but in an opposite direction) as the first concave mirror. However, the additional component and the additional steps needed to fabricate this arrangement would result in a higher cost for the device. Additionally, there is a lack of machinery which is optimized for fabricating such assemblies and therefore the symmetrical disk approach can involve extra time in manufacturing in addition to the extra materials.

Another potential shortcoming with the symmetrical disk approach is that it can also be complex to resolve or correct for residual errors in manufacturing, which are virtually unavoidable for such an arrangement. Such errors generate vibrations, which need to be corrected. These types of errors are inherently difficult to correct because the assembly needs to be stopped in order to be adjusted, but the motor must be spinning in order to observe the vibration. Furthermore, making the necessary adjustments can be very time consuming.

As discussed above, methods of scanning a laser beam to perform measurements typically involve the mechanical movement of an optical device. For retinal birefringence scanning, there is a mirror that is both tilted and spinning at a high speed (e.g. 12,000 rpm). When utilizing mechanical movements of optical devices, vibrations can present significant complexities to scanning instruments. The vibrations must be kept low enough so as not to impact the measurements intended by the instrument.

There are other complications with using mechanical movements for scanning optical instruments, such as:

Lifetime of the assembly—the useful lifetime of the instrument is often limited by the life span of the motor, which has a shorter life span than virtually every other component of the optical scanning instrument.

Fabrication/Assembly—Regarding the fabrication/assembly of the instrument, the process is not likely to be automated. Rather, highly skilled personnel are likely needed to assemble the components to the tight tolerances needed to achieve the necessary balance and to make adjustments to minimize vibrations—all which lead to higher than optimal costs.

Noise—even relatively quiet motors will make an audible sound that can be distracting to a patient.

Safety/Durability—From a robustness perspective, any time a component (e.g., the motor, the shaft and/or the mirror) is spinning at such a high speed (such as 12,000 rpm), the component is more susceptible to failure (e.g., due to fatigue) and such failure can potentially cause significant damage to the instrument.

Cost—the combination of the above issues generates significant requirements on the design of the instrument that add time and materials to the production process, increasing overall cost.

DETAILED DESCRIPTION

It is to be understood that at least some of the figures and descriptions of the invention have been simplified to illustrate elements that are relevant for a clear understanding of the invention, while eliminating, for purposes of clarity, other elements that those of ordinary skill in the art will appreciate may also comprise a portion of the invention. However, because such elements are well known in the art, and because they do not facilitate a better understanding of the invention, a description of such elements is not provided herein.

The inventors have identified a need for a system which measures fixation and which does not require any scanning mechanisms or mechanical movement of an optical device.

Many of the problems associated with the scanning method can be reduced by altering the method of sensing, and transitioning the design to the use of an imager to capture, within a single image, the entire information required to determine fixation.

Figure 1:
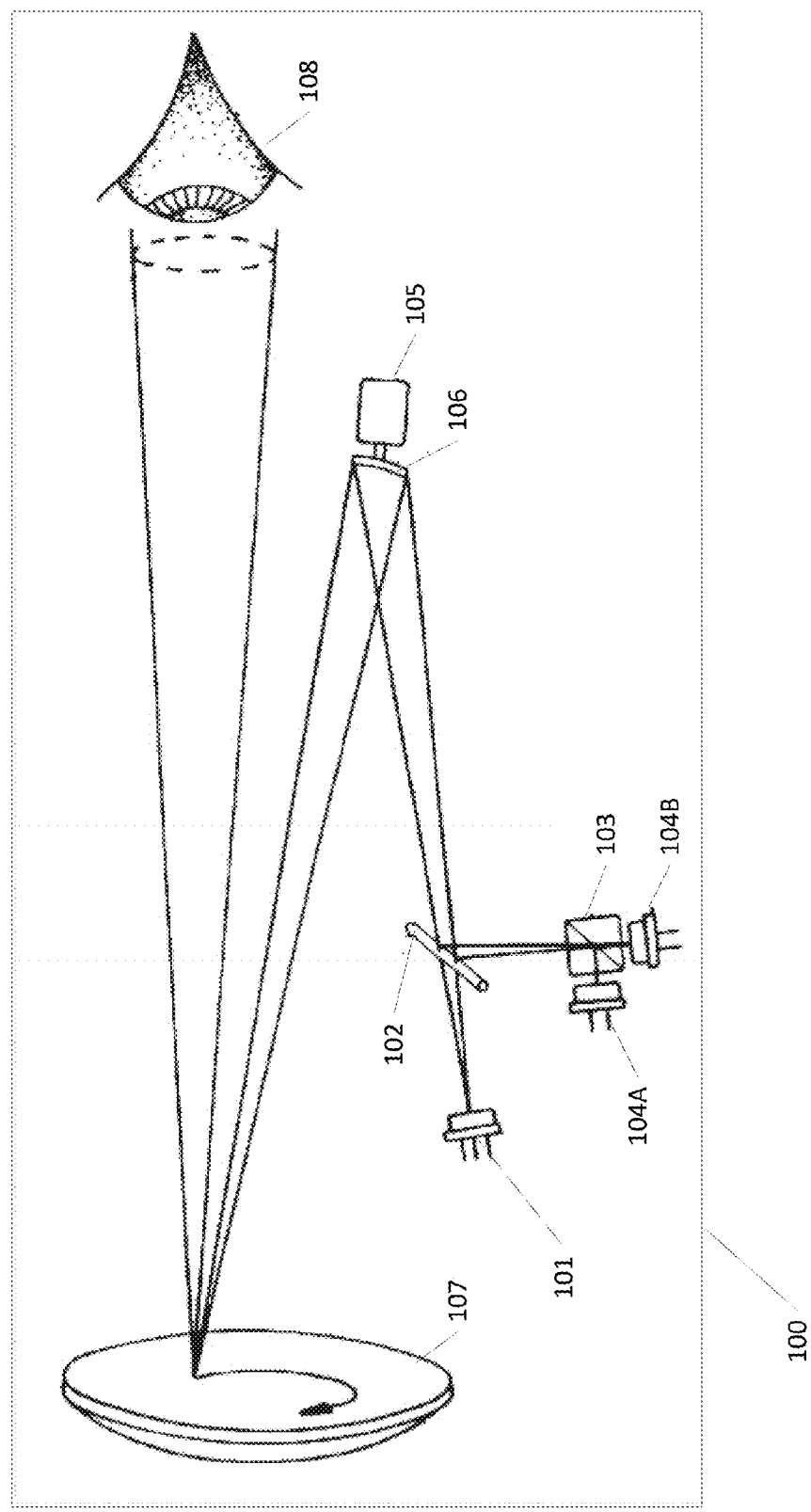
FIG. 1 illustrates a device for assessing the direction of fixation of an eye.
Figure 2:
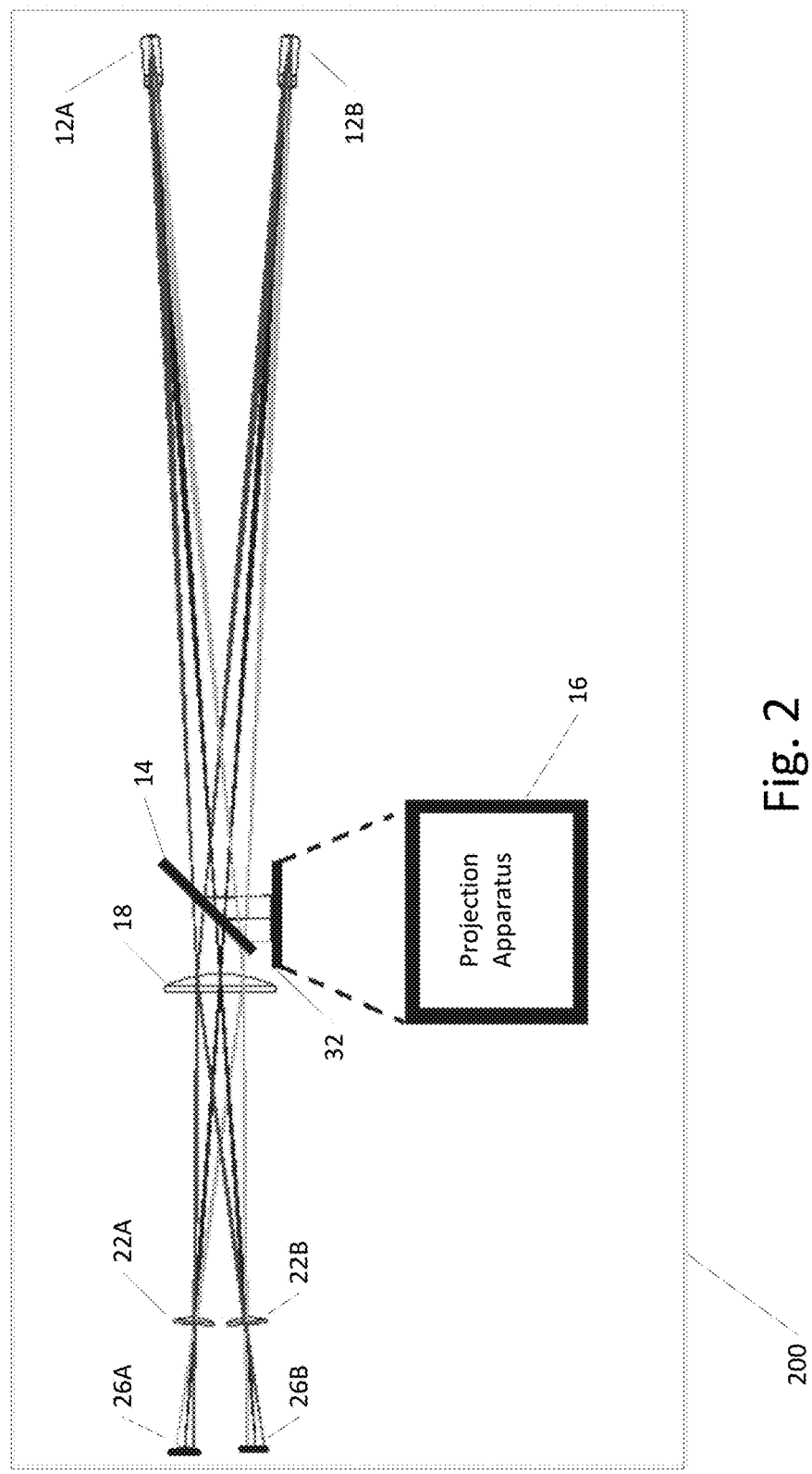
FIG. 2 illustrates an apparatus for fixation measurement according to an exemplary embodiment.

FIG. 2 illustrates an apparatus 200 for fixation measurement according to an exemplary embodiment. As shown in FIG. 2, the apparatus 100 includes a polarizing beam splitter 14, a projection apparatus 16, a convex lens 18, focusing lenses 22A and 22B, and image sensing devices 26A and 26B. As will be described in greater detail below, apparatus 200 utilizes an image-based scanning method to measure fixation. By using an image-based scanning method, the above-described components of the apparatus 200 may be fixed in place—they do not need to move or rotate.

The polarizing beam splitter 14 can be any suitable type of beam splitter. The image projection apparatus 16 is configured to generate a stimulus and project the generated stimulus to a projection plane 32 which is positioned below the beam splitter 14. Since this stimulus is the target fixation point for the patient who is being examined and, the stimulus can also be referred to as the target image.

Referring back to FIG. 2, the convex lens 18 may be any suitable type of convex lens and operates as a pupil reimaging lens. The focusing lenses 22A and 22B can be any suitable type of convex lenses, and can be selected based on the types of image analysis to be performed. Focusing lens 22A is associated with a first eye 12A of a person (such as a patient) and focusing lens 22B is associated with a second eye 12B of the person.

The image sensing devices 26A and 26B may be any suitable type of image sensing device. For example, according to various embodiments, the image sensing devices 26A and 26B can be charge coupled device (CCD) image sensors, complementary metal-oxide-semiconductor (CMOS) image sensors, etc. The image sensing devices 26A and 26B can be selected based on the desired image size and the focal length of the second and third convex lenses 22A and 22B. The first image sensing device 26A is associated with a first eye 12A of the person and the second image sensing device is associated with a second eye 12B of the person. The image sensing devices 26A and 26B can be utilized to capture, with a single image, the entire information contained from a single scan.

Figure 4:
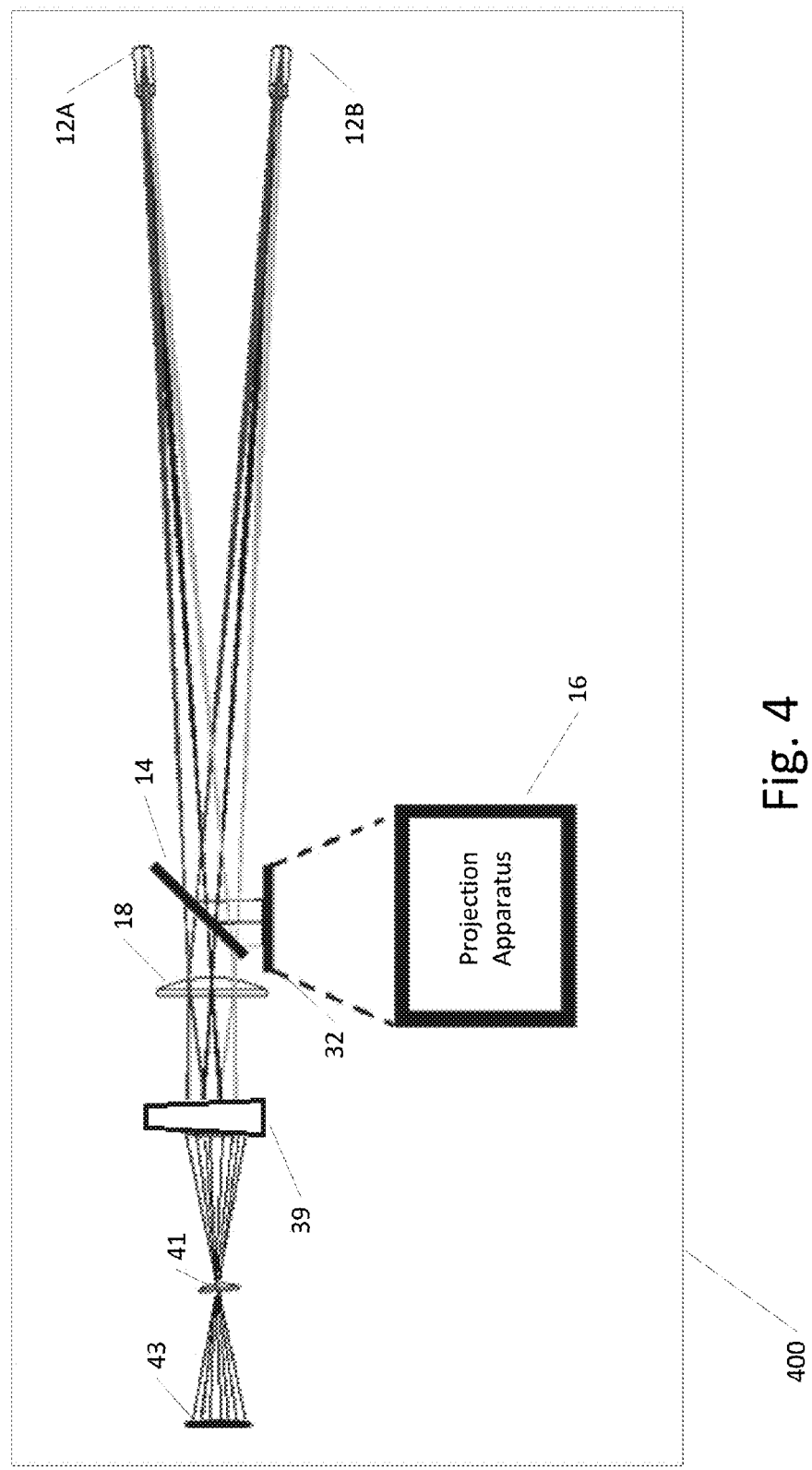
FIG. 4 illustrates another apparatus for fixation measurement according to an exemplary embodiment.

The apparatus 200 can also be configured so that light reflected from both of the eyes 12A and 12B meets at a single convex lens and is imaged onto a single image sensing device. An example of this is shown in apparatus 400 of FIG. 4, which is similar to the apparatus 200 of FIG. 2, except that focusing lenses 22A and 22B are replaced by a single convex lens 41, image sensing devices 26A and 26B are replaced by a single image sensing device 43, and prism 39 is added to focus reflected light onto lens 41.

In operation, the projection apparatus 16 utilizes laser light to generate the target image, and the projection apparatus projects the target to the projection plane 32. When a person (hereinafter referred to as a patient) positions his or her eyes 12A and 12B to look into the apparatus 200 and at the target (which appears to the patient to be in a direct line of sight), light representative of the target image is instantaneously imaged onto the patient's eyes 12A and 12B (onto the retinas of the eyes). The projection apparatus is thereby configured to project the generated target image onto one or more eyes of a patient.

Light representative of the target enters the patient's eyes 12A and 12B and a portion of this light is reflected off the fundus of each eye. The reflected light passes back out the patient's eyes 12A and 12B, through the beam splitter 14, through the first convex lens 18, through the focusing lenses 22A and 22B and onto the image sensing devices 26A and 26B, which are conjugate to the patient's retinas. The convex lens 18 operates to converge the light onto the focusing lenses 22A and 22B. The specific position of the focusing lenses 22A and 22B can be determined by the requirements of the apparatus 200, such as overall size, allowable sensor locations, etc. The focusing lenses 22A and 22B can be considered exit pupils, and operate to focus the reflected light onto the image sensing devices 26A and 26B, which then capture the reflected image reflected from the one or more eyes in response to the target image. As is discussed further below, the reflected image includes information indicating the fixation of the one or more eyes.

As shown in FIG. 2, apparatus 200 includes a polarizer in the form of polarizing beam splitter 14 which is configured to polarize light projected onto the one or more eyes 12A and 12B as part of the target image and configured to polarize light reflected from the one or more eyes as part of the reflected image.

Figure 3:
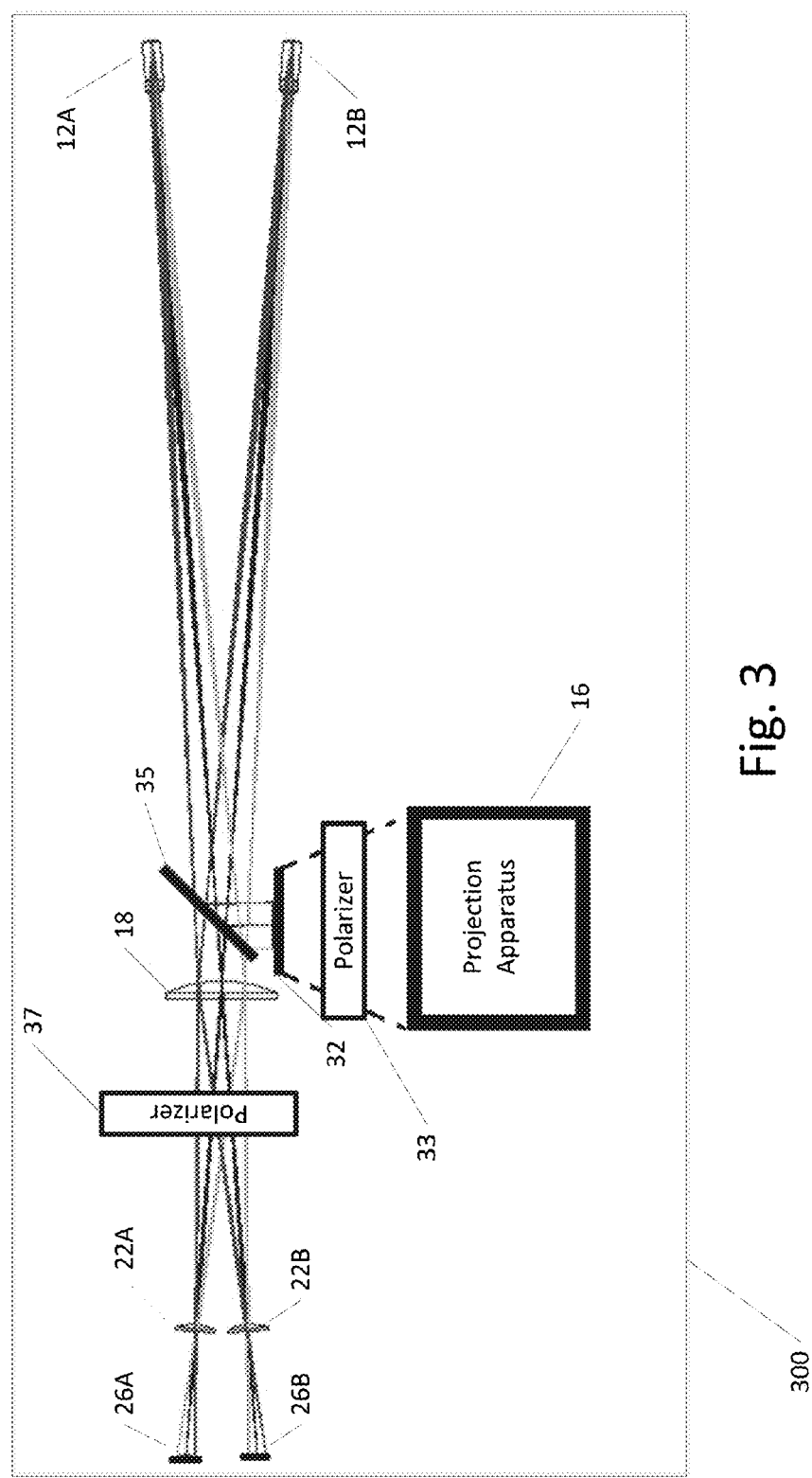
FIG. 3 illustrates another apparatus for fixation measurement according to an exemplary embodiment.
Figure 5:
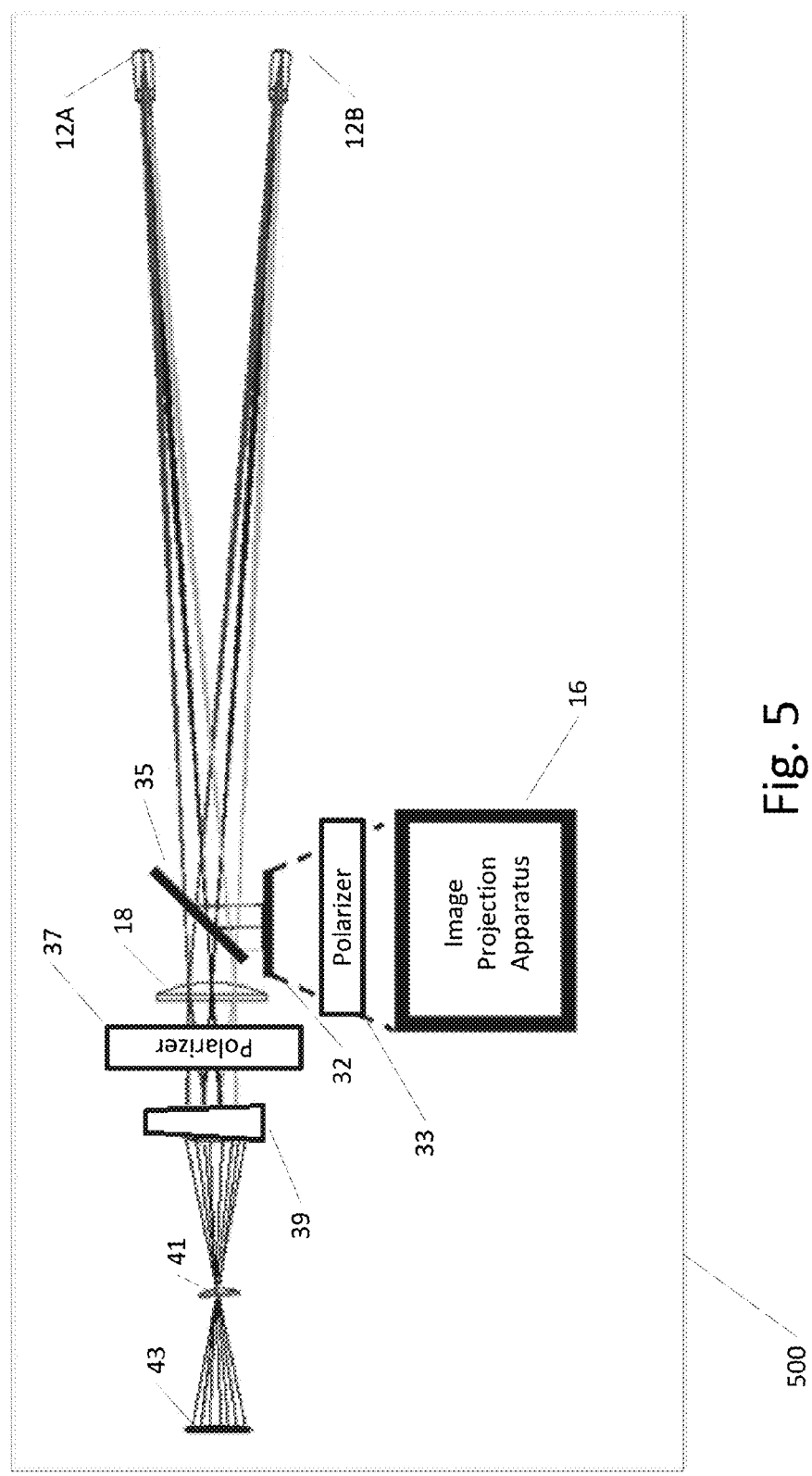
FIG. 5 illustrates another apparatus for fixation measurement according to an exemplary embodiment.

Polarization can also be performed by multiple polarizers. For example, FIG. 3 illustrates an apparatus 300 which is similar to the apparatus 200 of FIG. 2, except that the polarizing beam splitter 14 of apparatus 200 is replaced with a non-polarizing beam splitter 35 and two new polarizers 33 and 37 are added. Polarizer 33 is configured to polarize light projected onto the one or more eyes as part of the target image and Polarizer 37 is configured to polarize light reflected from the one or more eyes as part of the reflected image. Additionally, FIG. 5 illustrates an apparatus 500 which is similar to the apparatus 300 of FIG. 3 but which replaces focusing lenses 22A and 22B with a single convex lens 41 and image sensing devices 26A and 26B with a single image sensing device 43. Polarizers 33 and 37 may be embodied as any suitable type of polarizer. For example, polarizer 37 can be a linear polarizer and can be a coating on the "back" of the first convex lens 18.

The apparatuses shown in FIGS. 2-5 can be used to generate a target image which is a ring image and which is instantaneously imaged onto the patient's eyes 12 (onto the retinas of the eyes). Although the following sections refer to a ring image or a disk image, the apparatuses disclosed herein can be used to project a target image of any suitable shape (e.g., ellipse, oval, etc.).

When the target image is a ring image, the imaging devices 26, 28, or 43 will capture the full ring image as it is reflected from the one or more eye. Therefore, all of the information contained within a typical scan can be captured in a single image. The apparatuses shown in FIGS. 2-5 can include one or more computing devices which can analyze the reflect ring image for statistics/attributes such as average intensity, maximum intensity, minimum intensity, and general size (arc length and angular position) of regions of the ring with above average, below average and average intensity. Fixation of the one or more eyes can be calculated based at least in part on one or more polarization-related changes between the target image and the reflected image (and specifically between the attributes of the target ring image and the reflected ring image).

The ring in the reflected image can provide one of two general types of characteristics which are used to determine fixation. For the first type, the ring image has two shorter arc regions that are dimmer than average, and two that are brighter than average. The two bright regions are roughly 180 degrees apart from each other, as are the two dim regions, with dim regions separating bright regions. This image constitutes a successful measurement of fixation. A minimum of two sequential image captures that are successful measurements of fixation indicate the person has successfully demonstrated ability to fixate in that eye. However, successful fixation must be measured in both eyes simultaneously to fully pass the test for fixation. It is therefore required that both eyes have at least two sequential successful fixation measurements (captured at the same times) in order to pass the test for fixation. Detection of only one eye fixating, indicating that the other eye is misaligned, is strongly suggestive of the abnormal condition known as strabismus, or misalignment of the eyes.

For the second type, the ring in the reflected image has a larger arc-length region that is bright, and there is only one such section. The ring likewise has one larger arc-length region that is dim, and there is only one. This image constitutes a failure to fixate, and indicates that scanning for fixation needs to continue. There are other image types that can result from the above-described image-based scanning method and apparatus, but which do not pertain to determining fixation.

Figure 6:
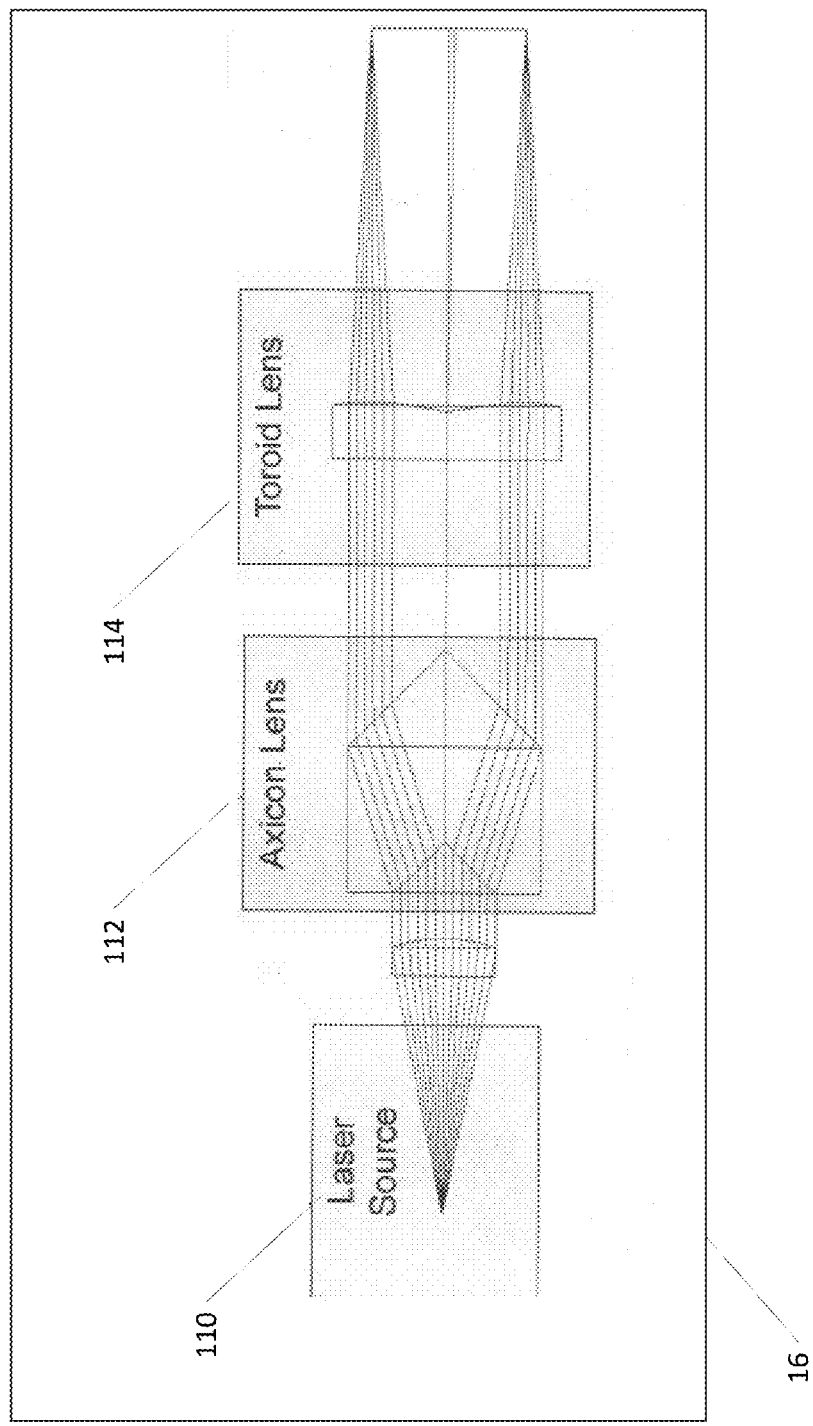
FIG. 6 illustrates a projection apparatus according to an exemplary embodiment.

The projection apparatus 16 shown in FIGS. 2-5 can take a variety of forms. For example, as shown in FIG. 6, the projection apparatus 16 can include a laser source 110, an axicon lens 112 and a toroid lens 114 which are utilized to generate and/or project the target ring image. By utilizing the axicon lens 112 in concert with the toroidal lens 114, a round target can be generated without the need for a rotating mirror. When using this projection apparatus, the optics are rotationally symmetric.

Figure 7:
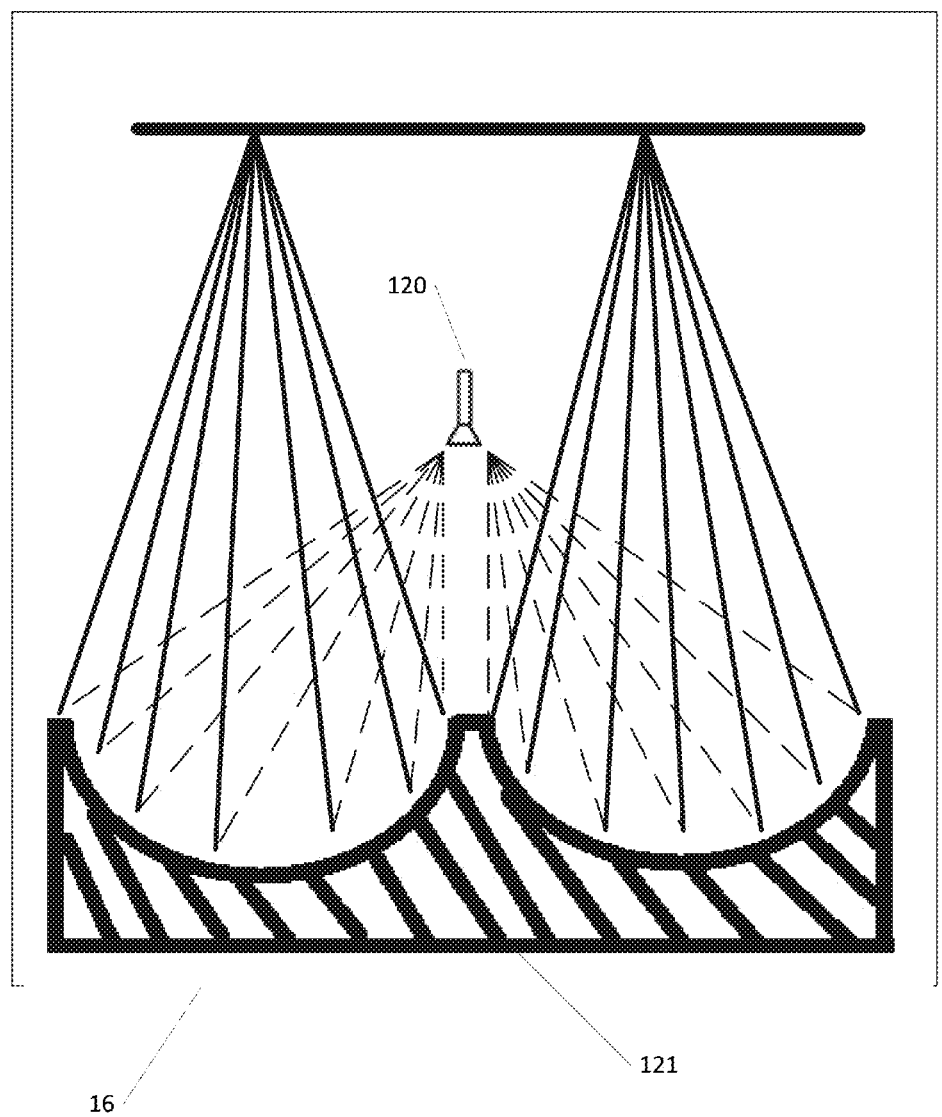
FIG. 7 illustrates another projection apparatus according to an exemplary embodiment.

Another possible projection apparatus is shown in FIG. 7. FIG. 7 illustrates a projection apparatus 16 including a light source 120 and a concave toroid mirror 121 facing the light source (shown as a cross section). The concave toroidal mirror 121 has a concave donut shape and is different from typical toroid shaped mirrors in that the shape is the "face" of the donut (toroid) containing the center rather than the "edge" of the donut (toroid). The concave toroidal mirror 121 is functionally similar to an axicon and is also used to generate and/or project the target ring image. The dashed lines indicate light projected from the light source 121 onto the mirror 121 and the solid lines indicate the reflected light from the mirror 121.

Figure 8A:
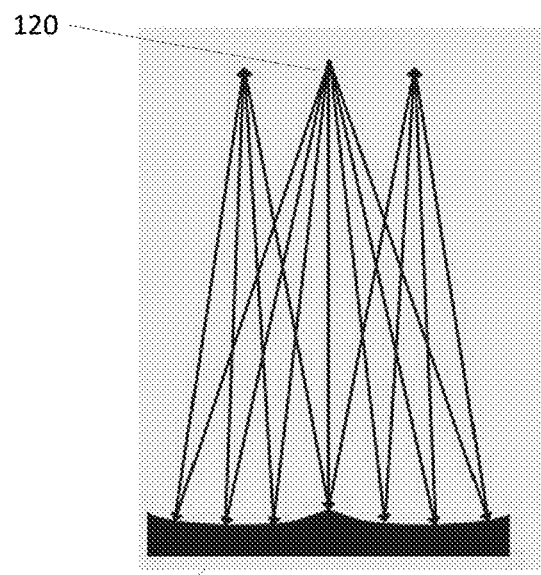
FIGS. 8A-8B illustrates addition features of the projection apparatus of FIG. 7 according to an exemplary embodiment.
Figure 8B:
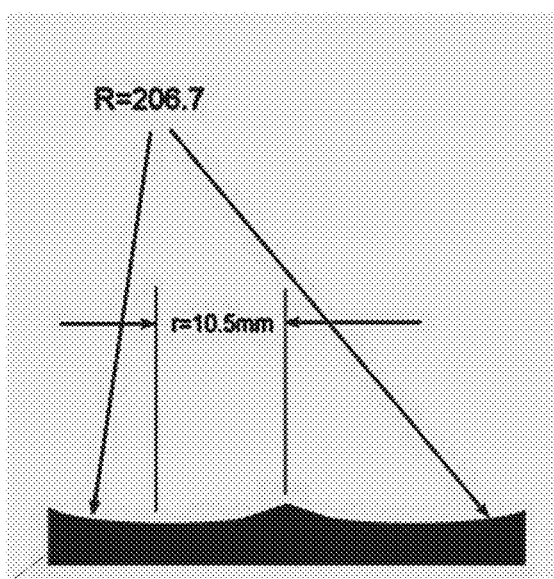

FIGS. 8A-8B illustrate additional views of the concave toroidal mirror 121. FIG. 8A also illustrates the path of light from the light source 120 to mirror 121 and reflected from the mirror 121. FIG. 8B illustrates some possible attributes of the concave toroidal mirror 121. In addition to the shown attributes, the mirror can have the following attributes:

Radius of curvature: 206.7
Vertex is off-center: 10.5 mm
Axis of rotation is at center
Outside diameter: 50 mm
Thickness (edge): 10 mm
Fabrication technique: diamond-turned aluminum Additionally or alternatively, the projection apparatus 16 can include a holographic device which is utilized to generate and/or project the target. The projection apparatus 16 can also include diffuse media in lieu of lenses.

Figure 9:
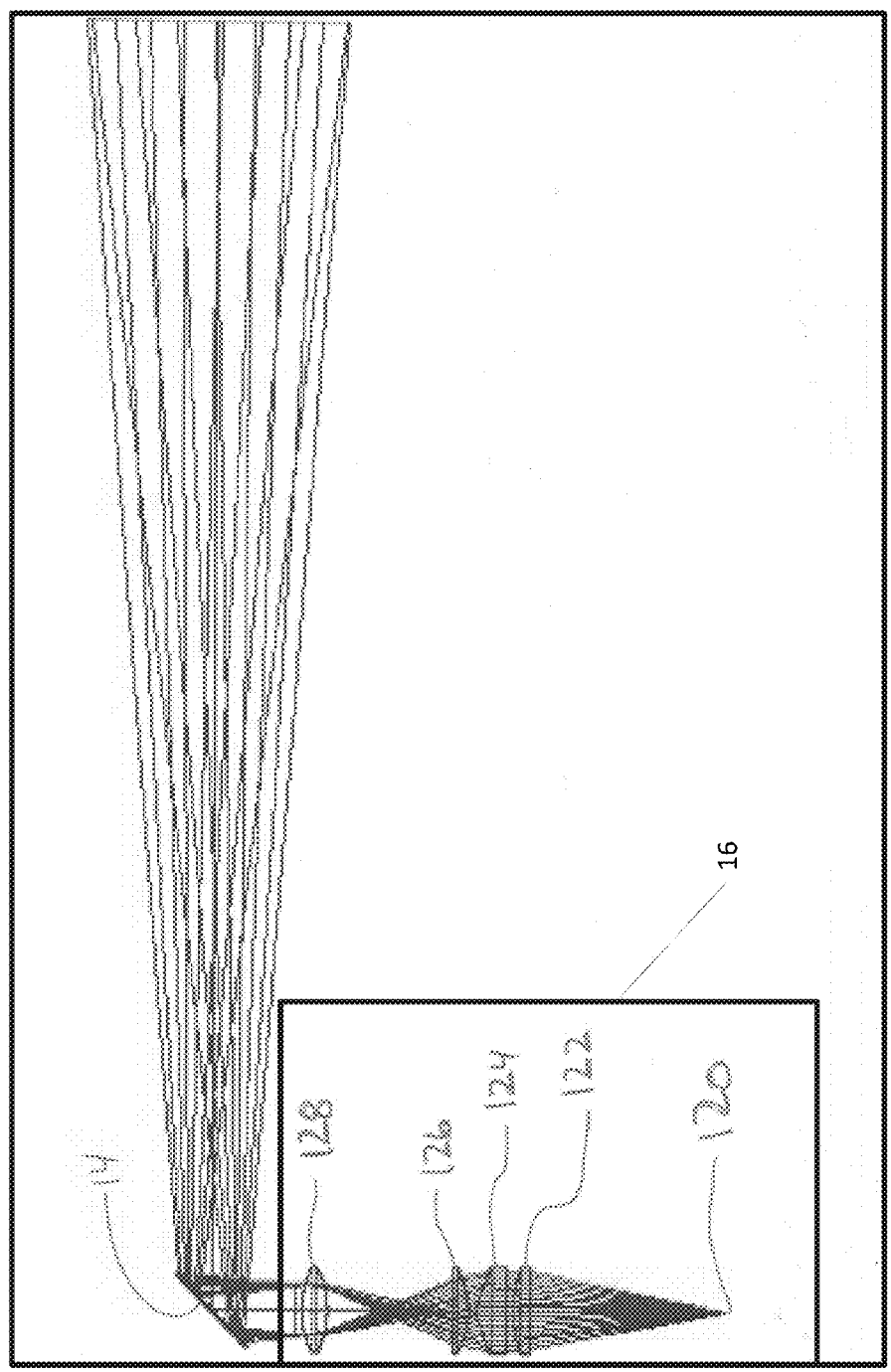
FIG. 9 illustrates another projection apparatus according to an exemplary embodiment.

Additionally, as shown in FIG. 9, the projection apparatus 16 can include a light source (e.g., a diode laser), a first plano-convex lens, an axicon lens and a second plano-convex lens. As shown in FIG. 9, the projection apparatus 16 includes a light source 120, a first plano-convex lens 122, an axicon lens 124 and a second plano-convex lens 126. The light source 120 may be any suitable type of light source. For example, the light source 120 can be a diode laser. The axicon lens 124 is positioned between the first and second plano-convex lenses 122, 126. When using this projection apparatus, the target is immersed in the bi-convex lens 128, but the appearance of the target from the perspective of the patient will be "behind" the beamsplitter 14.

Figure 10:
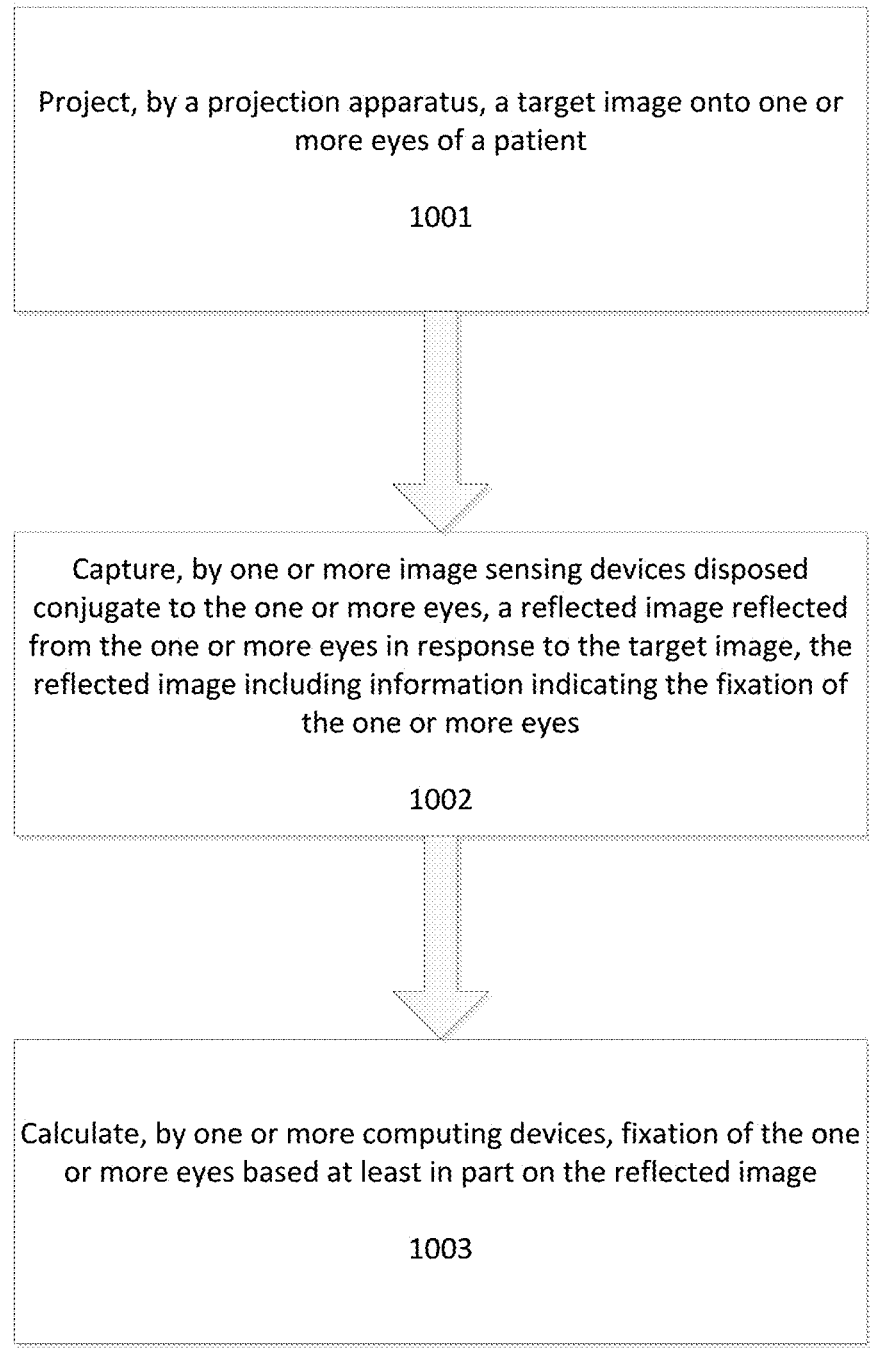
FIG. 10 illustrates a flowchart for fixation measurement according to an exemplary embodiment.

FIG. 10 illustrates a flowchart for a method of fixation measurement which can be performed using any of the disclosed apparatuses. At step 101 a target image is projected onto one or more eyes of a patient by a projection apparatus. At step 102 a reflected image reflected from the one or more eyes in response to the target image is captured by one or more image sensing devices disposed conjugate to the one or more eyes. The reflected image includes information indicating the fixation of the one or more eyes. Additionally, at step 103 the fixation of the one or more eyes is calculated based at least in part on the reflected image.

A benefit of using an image-based approach is the ability to choose the integration time for the image exposure. The time of the exposure ideally should be as short as possible to minimize the effects of background signals. The shorter the integration time, the less background light that will be measured. By having the entire visual stimulus (of the target ring image, for example) be imaged at once, it is possible to have the illumination be performed with a pulsed laser. The pulse can be substantially bright enough to provide significant signal during even very short integration times. This allows for a means to achieve very high signal to noise ratio, improving the image processing algorithm accuracy. The shorter exposure time also permits a better sampling of the retina during a scan, as it greatly reduces the amount of movement that is possible during a sampling interval. Compared with a scanning technique operating at 200 Hz, which would require 5 ms to achieve a single revolution scan (and multiple scanner rotations are required to establish the frequencies that need to be measured), an image can be captured in much less than a millisecond (for example, 10 us) and all the information is contained within that single image Aside from alleviating the problems associated with polarization and mechanical scanning, there are many additional benefits of the disclosed apparatus and method.

Images can be stored, and these are likely to offer clinical benefits as the patient ages. Any changes as a function of age would not be limited to a "pass" or "fail". An ophthalmologist would have an opportunity to review the images and determine if there is any other useful information. For example, the magnitude of the fixation error can be estimated.

Images can be analyzed to determine the nature of the stray light, possibly allowing further investigation into methods of reducing noise.

The imagers used to determine fixation are likely to be very useful to measure other optical characteristics of the eyes, given the appropriate design. Most notable is the desire to measure refraction error in each eye, such as astigmatism, nearsightedness, or farsightedness.

Using an imager-based method of measuring birefringence fixation allows image-based methods of also performing refraction error measurements.

As mentioned above, a significant benefit to using image based measurements for fixation measurements is the ability to repurpose the image sensors to measure refraction errors. Although the methodology for measuring refraction is somewhat different than what is required for measuring fixation, the lenses and image sensors can be designed to be common to both use cases. This offers a benefit to a medical professional because it reduces the number of instruments that are needed to achieve a full examination of the patient, whether the medical professional is a pediatrician or an ophthalmologist.

Figure 11:
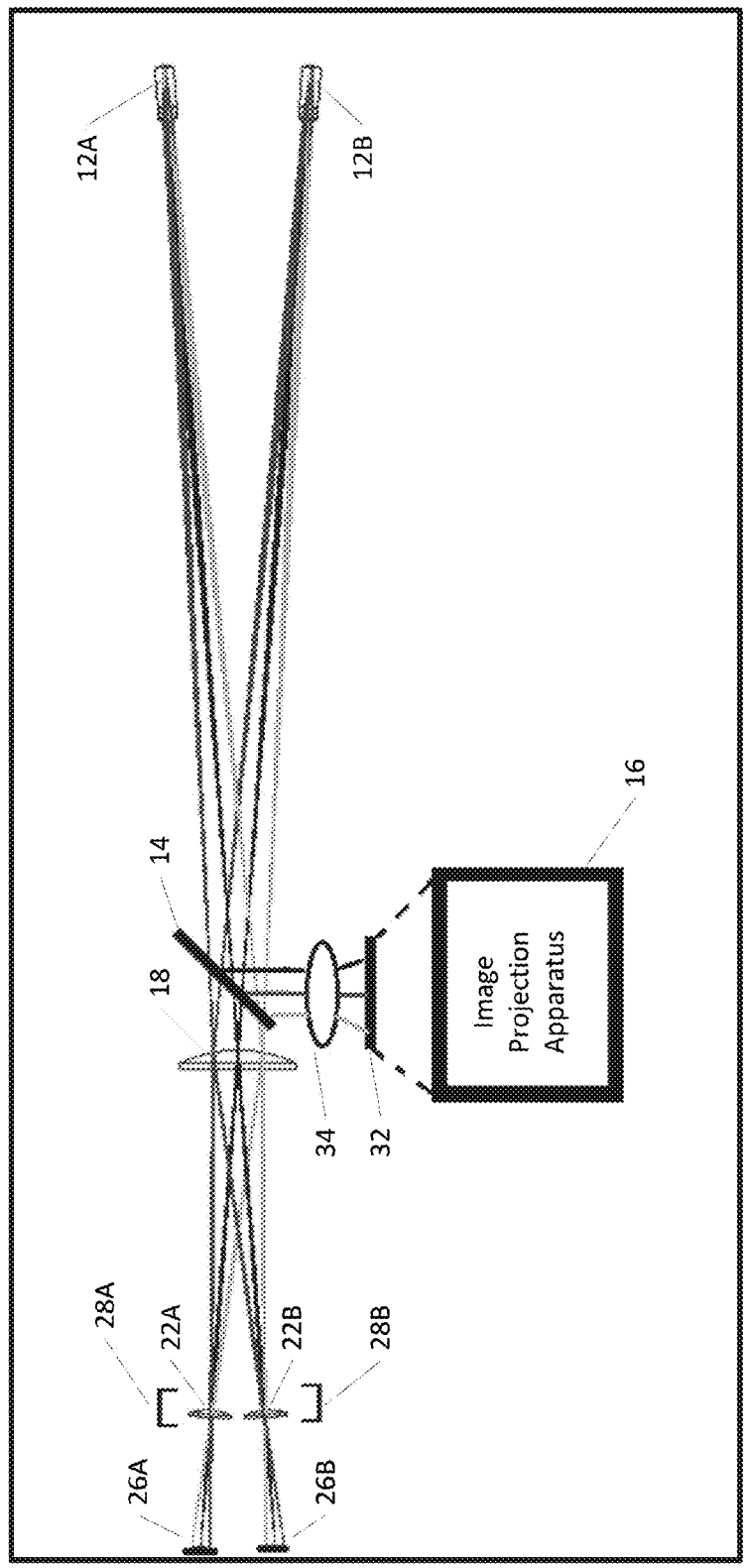
FIG. 11 illustrates an apparatus for refractive error measurement according to an exemplary embodiment.

An apparatus for measurement of refractive error is shown in FIG. 11. Many of the components shown in FIG. 11 are similar to those of the apparatus of FIG. 2, including image projection apparatus 16, beam splitter 14, convex lens 18, focusing lenses 22A and 22B, and image sensing devices 26A and 26B. The focusing lenses 22A and 22B and image sensing devices are also associated with one or more eyes of patient 12A and 12B.

The nominal range for retinal birefringence scanning is 400 mm, or 2.5 diopters. A typical patient would be accommodating to the target at this range. This would not sufficiently test a patients' ability to adjust refraction to accommodate objects at other distances. Therefore, an additional lens 34 can be added to the instrument between the viewing target and the patients' eyes 12A and 12B. This lens 34 can be positioned into place by the medical professional performing the refraction measurement (for example, by means of a cartridge that is pushed into place for the refraction measurement, but pulled out of place for the fixation measurement). The lens 34 can have a focal length and be positioned such that it is at a distance from the target to make the target appear as if it is located many meters in range (nominally less than $\frac{1}{10}^{th}$ diopter) and further away than it actually is.

During measurement of refraction, the image sensing devices 26A and 26B can capture images while the focusing lenses 22A and 22B that lie immediately in front of the image sensing devices 26A and 26B can be adjusted for focus. The focusing lenses 22A and 22B can be configured to be displaced along an axis by a focusing mechanism (not shown) to thereby alter the one or more reflected images captured by the one or more image sensing devices. For example, as shown in FIG. 5, focusing lens 22A can be displaced along the range shown by 28A and focusing lens 22B can displaced along the range shown by 28B.

The focus mechanism can be manufactured such that changes in the displacement of each focusing lens are well-correlated with known levels of refraction error. One common way to achieve this is to simply measure the position of the focus mechanism in microns. The number of microns that the focus mechanism is shifted from the nominal (no refractive error) position tells the amount of refraction error that is being measured. Therefore, based on the position of the focus mechanism that is required to achieve the best conjugate image of the retina, the patients' spherical refraction error can be measured.

Figure 12:
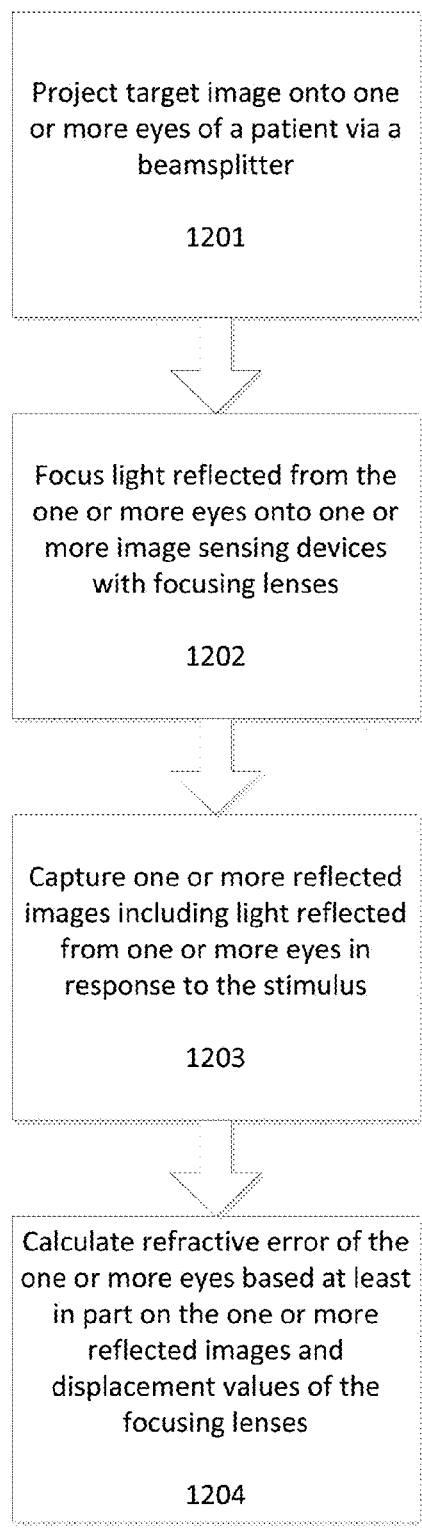
FIG. 12 illustrates a flowchart for refractive error measurement according to an exemplary embodiment.

FIG. 12 illustrates a flowchart for a method of refractive error measurement according to an exemplary embodiment. The method, or steps in the method, can be performed using an apparatus such as the one described with reference to FIG. 11.

At step 1201 a stimulus (target image) is projected by an image projection apparatus onto one or more eyes of a patient via a beam splitter. A lens can be disposed between the stimulus and the one or more eyes which has a focal length and position relative to the stimulus (target) such that the stimulus (target) appears to the patient to be further away than it is.

To measure astigmatism, the target being imaged would preferentially have features that would assist in the determination of this type of error. One example target would be comprised of a series of pairs of short lines, spaced every 3 degrees. An example of this type of target is similar to a watch dial, although rather than each minute marker being just one line, it would consist of a double line. The angular diameter of this "watch dial" target would nominally be approximately the same diameter as that used for measuring fixation error, or about 3 degrees (1.5 degrees from center to edge). The series of double lines in this manner would appear during an exam as being entirely in-focus at a particular focus setting for a patient with no astigmatism. However, if the patient has astigmatism, there will be regions where the double-lines will smear due to the astigmatism error. The location of the lines that smear will also indicate the axis of the astigmatism error. As the focus mechanism is adjusted (preferentially using an automated procedure), the location of the double-lines that are in focus and out of focus will shift for a patient that has astigmatism. There will be a focus position that provides best sharpness for some lines, while the others are out of focus. Further adjustment of the focus mechanism will alter this, however, and the lines that were previously smeared will become sharply focused. Additionally, the lines that were previously well focused will then become smeared (nominally the groups of lines that are in best focus and those with the most smear will be at 90 degrees to each other). Measuring the focus shift required to achieve best focus for all of these lines will tell the magnitude of the astigmatism, whereas the midpoint between these (the position at which virtually all sets of line will be similarly smeared) will be the average refraction error.

Another method is to simply use two concentric rings, closely spaced. A patient with astigmatism will exhibit images with the rings resolved in two locations, directly opposite of each other with respect to the center of the ring. The remaining sections of the ring will be smeared. As focus is shifted, the regions where the ring is optimally resolved will shift roughly 90 degrees. By recording the shift in focus between these two cases, the astigmatism refraction error can be measured, as can the axis of the error as determined by the locations where the ring is resolved as focus is changed. A target image comprised of a double ring is preferable due to its ability to be used for both fixation and refraction measurements.

At step 1202 one or more focusing lenses disposed between one or more image sensing devices and the one or more eyes are used to focus the light reflected from the one or more eyes onto the one or more image sensing devices. As discussed above, the one or more focusing lenses are configured to be displaced along an axis by one or more focusing mechanisms to thereby alter one or more reflected images captured by the one or more image sensing devices. The displacement of each of the focusing lenses can be recorded, stored, or otherwise tracked as displacement values.

At step 1203 one or more image sensing devices disposed conjugate to the one or more eyes capture the one or more reflected images including light reflected from the one or more eyes in response to the stimulus (target).

At step 1204 the refractive error in at least one of the one or more eyes is calculated by one or more computing devices based at least in part on the one or more reflected images and one or more displacement values of at least one of the one or more focusing lenses. Each of the one or more displacement values can correspond to a different reflected image in the one or more reflected images. As discussed earlier, the displacement amount corresponding to the reflected image which best resolves the target image can be used to determine the refractive error in an eye (such as by correlating the displacement amount with known levels of refractive error).

Figure 13:
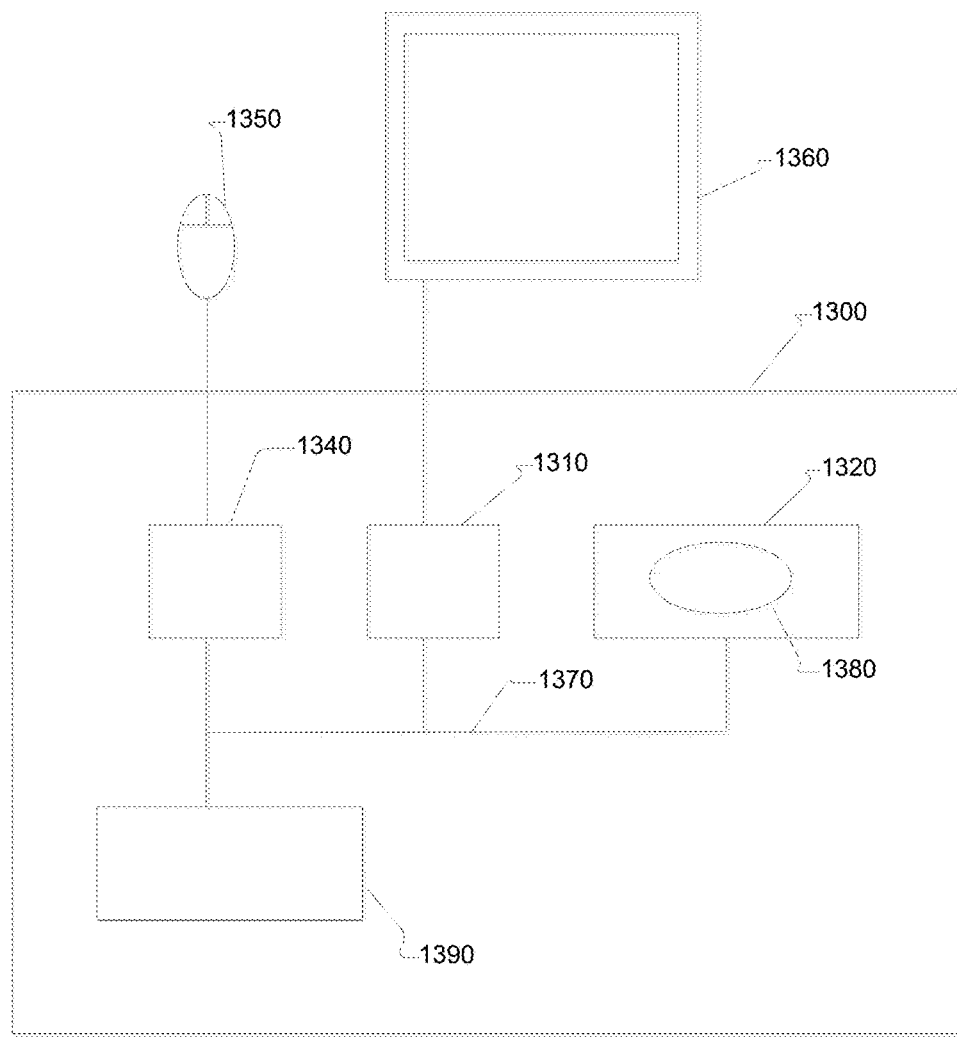
FIG. 13 illustrates an exemplary computing environment that can be used to carry out at least part of the methods disclosed herein.

One or more of the above-described techniques can be implemented in or involve one or more computer systems. FIG. 13 illustrates a generalized example of a computing environment 1300. The computing environment 1300 is not intended to suggest any limitation as to scope of use or functionality of a described embodiment.

With reference to FIG. 13, the computing environment 1300 includes at least one processing unit 1310 and memory 1320. The processing unit 1310 executes computer-executable instructions and may be a real or a virtual processor. In a multi-processing system, multiple processing units execute computer-executable instructions to increase processing power. The memory 1320 may be volatile memory (e.g., registers, cache, RAM), non-volatile memory (e.g., ROM, EEPROM, flash memory, etc.), or some combination of the two. The memory 1320 may store software instructions 1380 for implementing the described techniques when executed by one or more processors. Memory 1320 can be one memory device or multiple memory devices.

A computing environment may have additional features. For example, the computing environment 1300 includes storage 1340, one or more input devices 1350, one or more output devices 1360, and one or more communication connections 1390. An interconnection mechanism 1370, such as a bus, controller, or network interconnects the components of the computing environment 1300. Typically, operating system software or firmware (not shown) provides an operating environment for other software executing in the computing environment 1300, and coordinates activities of the components of the computing environment 1300.

The storage 1340 may be removable or non-removable, and includes magnetic disks, magnetic tapes or cassettes, CD-ROMs, CD-RWs, DVDs, or any other medium which can be used to store information and which can be accessed within the computing environment 1300. The storage 1340 may store instructions for the software 1380.

The input device(s) 1350 may be a touch input device such as a keyboard, mouse, pen, trackball, touch screen, or game controller, a voice input device, a scanning device, a digital camera, remote control, or another device that provides input to the computing environment 1300. The output device(s) 1360 may be a display, television, monitor, printer, speaker, or another device that provides output from the computing environment 1300.

The communication connection(s) 1390 enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Implementations can be described in the general context of computer-readable media. Computer-readable media are any available media that can be accessed within a computing environment. By way of example, and not limitation, within the computing environment 1300, computer-readable media include memory 1320, storage 1340, communication media, and combinations of any of the above.

Of course, FIG. 13 illustrates computing environment 1300, display device 1360, and input device 1350 as separate devices for ease of identification only. Computing environment 1300, display device 1360, and input device 1350 may be separate devices (e.g., a personal computer connected by wires to a monitor and mouse), may be integrated in a single device (e.g., a mobile device with a touch-display, such as a smartphone or a tablet), or any combination of devices (e.g., a computing device operatively coupled to a touch-screen display device, a plurality of computing devices attached to a single display device and input device, etc.). Computing environment 1300 may be a set-top box, mobile device, personal computer, or one or more servers, for example a farm of networked servers, a clustered server environment, or a cloud network of computing devices.

Having described and illustrated the principles of our invention with reference to the described embodiment, it will be recognized that the described embodiment can be modified in arrangement and detail without departing from such principles. It should be understood that the programs, processes, or methods described herein are not related or limited to any particular type of computing environment, unless indicated otherwise. Various types of general purpose or specialized computing environments may be used with or perform operations in accordance with the teachings described herein. Elements of the described embodiment shown in software may be implemented in hardware and vice versa.

What is claimed is:

1. An apparatus for fixation measurement, the apparatus comprising:
   a projection apparatus configured to project a target image onto one or more retinas of one or more eyes of a patient; and
   one or more image sensing devices disposed conjugate to the one or more retinas wherein the one or more image sensing devices are configured to capture a reflected image reflected from the one or more retinas in response to the target image and wherein the reflected image comprises a modified version of the target image as reflected from the one or more retinas and wherein one or more differences between the target image and the reflected image indicate fixation of the one or more eyes.

2. The apparatus of claim 1, further comprising:
   one or more computing devices configured to calculate fixation of the one or more eyes based at least in part on the reflected image.

3. The apparatus of claim 2, wherein the fixation of the one or more eyes is calculated based at least in part on one or more polarization-related changes between the target image and the reflected image.

4. The apparatus of claim 1, further comprising:
   a polarizer configured to polarize light projected onto the one or more retinas as part of the target image and configured to polarize light reflected from the one or more retinas as part of the reflected image.

5. The apparatus of claim 4, wherein the polarizer comprises a polarizing beam splitter.

6. The apparatus of claim 1, further comprising:
   a first polarizer configured to polarize light projected onto the one or more retinas as part of the target image; and
   a second polarizer configured to polarize light reflected from the one or more retinas as part of the reflected image.

7. The apparatus of claim 1, wherein the target image comprises a ring image.

8. The apparatus of claim 7, wherein the projection apparatus comprises:
   a light source configured to project light through an axicon lens to thereby generate a circular light projection; and
   a toroidal lens configured to focus the circular light projection into the ring image.

9. The apparatus of claim 7, wherein the projection apparatus comprises:
   a light source configured to project light; and
   a concave toroidal mirror configured to reflect the light projected from the light source into the ring image.

10. The method for fixation measurement, the method comprising:
    projecting, by a projection apparatus, a target image onto one or more retinas of one or more eyes of a patient; and
    capturing, by one or more image sensing devices disposed conjugate to the one or more retinas, a reflected image reflected from the one or more retinas in response to the target image, wherein the reflected image comprises a modified version of the target image as reflected from the one or more retinas and wherein one or more differences between the target image and the reflected image indicate fixation of the one or more eyes.

11. The method of claim 10, further comprising:
    calculating, by one or more computing devices, fixation of the one or more eyes based at least in part on the reflected image.

12. The method of claim 11, wherein the fixation of the one or more eyes is calculated based at least in part on one or more polarization-related changes between the target image and the reflected image.

13. The method of claim 10, further comprising:
    polarizing, by a polarizer, light projected onto the one or more retinas as part of the target image; and
    polarizing, by the polarizer, light reflected from the one or more retinas as part of the reflected image.

14. The method of claim 13, wherein the polarizer comprises a polarizing beam splitter.

15. The method of claim 10, further comprising:
    polarizing, by a first polarizer, light projected onto the one or more retinas as part of the target image; and
    polarizing, by a second polarizer, light reflected from the one or more retinas as part of the reflected image.

16. The method of claim 10, wherein the target image comprises a ring image.

17. The method of claim 16, wherein the projection apparatus comprises:
    a light source configured to project light through an axicon lens to thereby generate a circular light projection; and
    a toroidal lens configured to focus the circular light projection into the ring image.

18. The method of claim 16, wherein the projection apparatus comprises:
    a light source configured to project light; and
    a concave toroidal mirror configured to reflect the light projected from the light source into the ring image.

19. An apparatus for fixation measurement of a patient for screening for strabismus, the apparatus comprising:
    a projection apparatus configured to project a target image onto two retinas of two eyes of a patient;
    two or more image sensing devices disposed conjugate to the two retinas, wherein the two or more image sensing devices are configured to capture two reflected images reflected from the two retinas in response to the target image, wherein each of the two reflected images comprises a modified version of the target image as reflected from a corresponding retina, wherein one or more differences between the target image and each of the two reflected images indicate a direction of fixation of each of the two eyes, and wherein a misalignment in the direction of fixation of the two eyes corresponds to strabismus.

20. A method for fixation measurement of a patient for screening for strabismus, the method comprising:
    projecting, by a projection apparatus, a target image onto two retinas of two eyes of a patient; and
    capturing, by two or more image sensing devices disposed conjugate to the two retinas, two reflected images reflected from the two retinas in response to the target image, wherein each of the two reflected images comprises a modified version of the target image as reflected from a corresponding retina, wherein one or more differences between the target image and each of the two reflected images indicate a direction of fixation of each of the two eyes, and wherein a misalignment in the direction of fixation of the two eyes corresponds to strabismus.

21. An apparatus for refractive error measurement, the apparatus comprising:
    a projection apparatus configured to project a target image onto one or more retinas of one or more eyes of a patient;
    a lens disposed between the target image and the one or more eyes, the lens having a focal length and position relative to the target image such that the target image appears to the patient to be further away than it is;
    one or more image sensing devices disposed conjugate to the one or more retinas, wherein the one or more image sensing devices are configured to capture one or more reflected images including light reflected from the one or more retinas in response to the target image;
    one or more focusing lenses disposed between the one or more image sensing devices and the one or more eyes, wherein the one or more focusing lenses are configured to focus the light reflected from the one or more retinas onto the one or more image sensing devices, wherein the one or more focusing lenses are configured to be displaced along an axis to thereby alter the one or more reflected images captured by the one or more image sensing devices, and wherein a displacement of the one or more focusing lenses required to best resolve the one or more reflected images corresponds to a refractive error in the one or more eyes.

22. The apparatus of claim 21, further comprising:
    one or more computing devices configured to calculate refractive error in at least one of the one or more eyes based at least in part on the one or more reflected images and one or more displacement values of at least one of the one or more focusing lenses, wherein each of the one or more displacement values corresponds to a reflected image in the one or more reflected images.

23. A method for measurement of refractive error, the method comprising:
    projecting, by a projection apparatus, a target image onto one or more retinas of one or more eyes of a patient, wherein a lens disposed between the target image and the one or more eyes has a focal length and position relative to the target image such that the target image appears to the patient to be further away than it is;
    focusing, by one or more focusing lenses, light reflected from the one or more retinas onto one or more image sensing devices disposed conjugate to the one or more retinas, wherein the one or more focusing lenses are configured to be displaced along an axis to thereby alter one or more reflected images captured by the one or more image sensing devices, and wherein a displacement of the one or more focusing lenses required to best resolve the one or more reflected images corresponds to a refractive error in the one or more eyes; and
    capturing, by the one or more image sensing devices disposed conjugate to the one or more retinas, the one or more reflected images including light reflected from the one or more retinas in response to the target image.

24. The method of claim 23, further comprising:
    calculating, by one or more computing devices, refractive error in at least one of the one or more eyes based at least in part on the one or more reflected images and one or more displacement values of at least one of the one or more focusing lenses, wherein each of the one or more displacement values corresponds to a reflected image in the one or more reflected images.

* * * * *